(12) United States Patent
Noronha et al.

(10) Patent No.: US 8,309,771 B2
(45) Date of Patent: Nov. 13, 2012

(54) TWO-STAGE, GAS PHASE PROCESS FOR THE MANUFACTURE OF ALKYLENE GLYCOL

(75) Inventors: Joseph C. Noronha, Charleston, WV (US); Elbert J. Campbell, Missouri City, TX (US); Brian T. Keen, Pinch, WV (US); Dick A. Nagaki, Sun Prairie, WI (US); Hwaili Soo, Charleston, WV (US); David A. Spears, Midland, MI (US); John F. Szul, Hurricane, WV (US)

(73) Assignee: Dow Technology Investments LLC, Midland, MI (US)

( * ) Notice: Subject to any disclaimer, the term of this patent is extended or adjusted under 35 U.S.C. 154(b) by 636 days.

(21) Appl. No.: 12/533,753

(22) Filed: Jul. 31, 2009

(65) Prior Publication Data

US 2010/0036176 A1 Feb. 11, 2010

Related U.S. Application Data

(60) Provisional application No. 61/086,306, filed on Aug. 5, 2008.

(51) Int. Cl.
*C07C 29/03* (2006.01)
(52) U.S. Cl. .......................... 568/860; 568/865; 568/867
(58) Field of Classification Search .................. 568/867, 568/860, 865
See application file for complete search history.

(56) References Cited

U.S. PATENT DOCUMENTS

| | | | |
|---|---|---|---|
| 2,770,656 A | 11/1956 | Pye | |
| 3,091,647 A | 5/1963 | Hamilton et al. | |
| 4,233,221 A | 11/1980 | Raines et al. | |
| 4,571,440 A | 2/1986 | Keen et al. | |
| 4,667,045 A | 5/1987 | Briggs et al. | |
| 4,701,571 A | 10/1987 | Soo et al. | |
| 4,761,394 A | 8/1988 | Lauritzen | |
| 4,766,105 A | 8/1988 | Lauritzen | |
| 4,808,738 A | 2/1989 | Lauritzen | |
| 4,820,675 A | 4/1989 | Lauritzen | |
| 4,833,261 A | 5/1989 | Lauritzen | |
| 4,908,343 A | 3/1990 | Bhasin | |
| 4,916,243 A | 4/1990 | Bhasin et al. | |
| 4,967,018 A | 10/1990 | Soo et al. | |
| 5,057,481 A | 10/1991 | Bhasin | |
| 5,059,481 A | 10/1991 | Lustig et al. | |
| 5,102,848 A | 4/1992 | Soo et al. | |
| 5,136,106 A | 8/1992 | King | |
| 5,187,140 A | 2/1993 | Thorsteinson et al. | |
| 5,260,495 A | 11/1993 | Forkner | |
| 5,504,053 A | 4/1996 | Chou et al. | |
| 5,698,719 A | 12/1997 | Gaffney et al. | |
| 5,770,746 A | 6/1998 | Cooker et al. | |
| 5,945,568 A | 8/1999 | Nagata et al. | |
| 6,511,938 B1 | 1/2003 | Liu et al. | |
| 6,953,766 B2 | 10/2005 | Edwards | |
| 7,319,156 B2 | 1/2008 | Yako et al. | |
| 7,459,589 B2 | 12/2008 | Ramakers | |
| 2009/0143627 A1 | 6/2009 | Van Kruchten et al. | |

FOREIGN PATENT DOCUMENTS

| | | |
|---|---|---|
| EP | 0318815 A1 | 6/1989 |
| GB | 793766 | 4/1958 |

*Primary Examiner* — Sikarl Witherspoon
(74) *Attorney, Agent, or Firm* — Whyte Hirschboeck Dudek SC

(57) ABSTRACT

A two-stage, gas phase process for manufacturing alkylene glycol (e.g., ethylene glycol) from an alkene (e.g., ethylene), oxygen and water, the process comprising the steps of:

(A) Contacting under gas phase, oxidation conditions gaseous alkene and oxygen over a heterogeneous oxidation catalyst to produce a gaseous oxidation product comprising alkylene oxide, water and unreacted alkene;

(B) Contacting under gas phase, hydrolysis conditions the gaseous oxidation product of (A) with added water over a heterogeneous hydrolysis catalyst to produce a gaseous alkylene glycol and unreacted alkene; and (C) Recycling the unreacted alkene of (B) to (A).

The hydrolysis catalyst is selected from the group consisting of hydrotalcites, metal-loaded zeolites, phosphates, and metal-loaded ion-exchanged molecular sieves. The process improves over the conventional two-stage process by the elimination of steps and equipment to recover and refine alkylene oxide, the use of less water in the hydrolysis reaction, and the elimination of the entire evaporation train used in the recovery of alkylene glycol.

20 Claims, 4 Drawing Sheets

TWO-STAGE, GAS PHASE PROCESS FOR THE MANUFACTURE OF ALKYLENE GLYCOL

CROSS REFERENCE TO RELATED APPLICATIONS

The present application claims priority to U.S. patent application Ser. No. 61/086,306 filed on Aug. 5, 2008, the entire content of which is incorporated by reference herein.

FIELD OF THE INVENTION

The invention relates to the manufacture of alkylene glycol. In one aspect, the invention relates to the gas phase oxidation of an alkene while in another aspect the invention relates to the manufacture of alkylene glycol by coupling the gas phase oxidation of an alkene to alkylene oxide with the gas phase hydrolysis of the alkylene oxide to alkylene glycol.

BACKGROUND OF THE INVENTION

The conventional process for manufacturing alkylene glycol from an alkene, oxygen (or air) and water is described in FIG. 1 in the context of manufacturing ethylene glycol. The first stage is the gas phase oxidation of ethylene over a heterogeneous catalyst to produce ethylene oxide (EO). In order to achieve the desired reaction selectivity and reduce the hazards associated with EO manufacturing, the EO concentration is limited in the outlet reaction gas stream. Only partial oxidation of ethylene per pass occurs and as a consequence, the reactor outlet gas contains not only EO, but also unreacted ethylene and oxygen and, among other things, byproduct carbon dioxide, water and parts per million levels of aldehydes, such as acetaldehyde. Ballast gas, typically methane or nitrogen, is also present in the EO reactor outlet.

Upon exiting the EO reactor, the gaseous stream is typically cooled in one or more heat exchangers (not shown) to transfer the heat contained in the EO reactor gas to other process streams to reduce the energy requirements in the overall process. Although the energy integration is advantageous, the extra residence time required to pass through the heat exchangers can increase the amount of unintended side reactions that occur in the EO reactor outlet gas due to the high reactivity of ethylene oxide thus forming increased levels of impurities such as aldehydic compounds, chloride-containing species and oxygenated species. After being cooled, the gas stream is passed to an EO absorption unit. In the EO absorber, a large excess of water, typically 8:1 weight ratio of water to ethylene oxide or higher, is used to absorb the EO in the EO reactor outlet gas. The unreacted ethylene, by-product carbon dioxide and other unabsorbed compounds are passed to a separation unit in which a portion of the carbon dioxide is separated from the EO-lean EO reactor outlet gas, and the remaining gas is recycled back to the EO reactor. This return of the unreacted ethylene, oxygen, ballast gas and the remaining other components to the EO reactor is known as the recycle gas loop.

EO and water from the EO absorber are typically preheated in an exchanger and passed as a single stream to an EO stripping unit in which EO is separated from the water by vaporization. The amount of energy required to strip EO from the water is high since such a large excess of water is required in the absorption step. The tails stream from the stripping unit, containing the vast majority of the water is cooled and recycled back to the EO absorption unit. The stripped EO is partially condensed and/or reabsorbed before some of the EO is refined by passing through one or more distillation columns, and then collected for storage, shipping or use.

The second stage of the process is the liquid phase hydrolysis of EO to ethylene glycol. In the conventional manufacturing of mono-ethylene glycol (MEG), refined EO is diluted with a 10-15 fold weight-by-weight (w/w) excess of water ($H_2O$) for a $H_2O$:EO molar ratio of 24:1 to 37:1, and then thermally hydrolyzed. In some instances, a solid catalyst may be used to improve the selectivity to the preferred product of MEG. The conventional uncatalyzed liquid-phase process produces an assortment of glycol products including the desired MEG (e.g., 90-91 wt %), di-ethylene glycol (DEG) (e.g., 8-9 wt %) and 1 wt % or less of other higher molecular weight glycols, although the exact distribution depends largely upon the ratio of water to ethylene oxide in the dilution step. MEG is further refined by first removing the large excess of water in multiple evaporators and then distilled in several columns under reduced pressure. Water removed from the glycol product is recycled back to the beginning of the process for admixture with EO before or at the time EO is fed to the glycol reactor. The large excess of water used in the liquid phase hydrolysis process requires a large amount of energy to drive the glycol/water separation.

While the liquid-phase EO reaction to MEG and other EO derivatives has been extensively studied, the gas-phase EO hydrolysis reaction has received relatively little study. In the mid 1980's and early 1990's, Union Carbide Corporation researchers investigated the gas phase hydrolysis of EO to MEG, e.g., U.S. Pat. Nos. 4,701,571 and 5,260,495. While several compounds demonstrated a high degree of selectivity to MEG at a hydrolysis ratio of 1 w/w or lower, the catalyst activities and catalyst lifetimes limited the commercial appeal of the technology at that time. Therefore new gas phase hydrolysis catalysts that provide high MEG selectivity with improved catalyst activity, catalyst lifetime, stability and operation versus the prior disclosed catalysts are desired. Additionally, a gas phase hydrolysis process that provides significant economic benefits and addresses the drawbacks with conventional EO/EG processes is needed, such as energy requirements and impurity generation.

BRIEF SUMMARY OF THE INVENTION

According to this invention, the conventional two-stage process for the manufacture of alkylene glycol is improved by the elimination of steps and equipment to recover and refine alkylene oxide. The process is also improved by the use of less water, and the elimination of the entire evaporation train used in the recovery of alkylene glycol. Moreover, the recycle gas loop is used for the benefit of both stages of the process. As a result both operating, e.g., energy, and capital costs are reduced. In addition, the inventive process significantly reduces the overall residence time of ethylene oxide in the system as compared to the conventional two-stage process. This leads to a significant reduction in undesirable side reactions and, subsequently, to a reduction in undesirable impurities and, in turn, a higher quality of MEG. The inventive process also significantly reduces the overall inventory of ethylene oxide in the system as compared to the conventional two-stage process leading to an inherently safer process since there is less of the highly reactive chemical to manage in an upset condition.

In a first embodiment, the invention is a two-stage, gas phase process for manufacturing alkylene glycol from an alkene, oxygen and water, the process comprising the steps of:

(A) Contacting under gas phase, oxidation conditions gaseous alkene and oxygen over a heterogeneous oxidation catalyst to produce a gaseous oxidation product comprising alkylene oxide, water and unreacted alkene;

(B) Contacting under gas phase, hydrolysis conditions the gaseous oxidation product of (A) with added water over a heterogeneous hydrolysis catalyst to produce a gaseous alkylene glycol and unreacted alkene; and (C) Recycling the unreacted alkene of (B) to (A).

The gas phase oxidation reactor or zone is close-coupled to the gas phase hydrolysis reactor or zone, i.e., the effluent of the oxidation reactor or zone passes directly to the hydrolysis reactor or zone without alkylene oxide recovery or refinement. Typically the effluent of the gas phase oxidation zone is essentially completely gaseous but in some embodiments of the invention, this effluent can comprise one or more liquid components which can be, and preferably are, gasified prior to being fed to the hydrolysis reactor or zone. In some embodiments the one or more gas phase components of the oxidation reactor or zone can be condensed prior to being fed to the hydrolysis reactor or zone, and such an effluent component can be fed either in a condensed (liquid) state or after first being re-gasified.

Although water is a byproduct of the oxidation of the alkene in step (A), typically insufficient water is produced for the maximum hydrolysis of alkylene oxide to alkylene glycol in step (B). As such, additional water (or steam), i.e., water other than the byproduct water already present in the gaseous oxidation product, is mixed with the gaseous oxidation product before the gaseous oxidation product is hydrolyzed in step (B). Steam condensate from other areas of the process can be used as the water feed, possibly even forming a water recycle loop within the process. The amount of water added is such that the water:alkylene oxide molar ratio is between 0.5:1 and 20:1 and in the case of the hydrolysis of ethylene oxide, preferably between 0.5:1 and 10:1. Liquid water and steam in combination can also be used to obtain the desired hydrolysis ratio and to obtain the desired inlet temperature to the hydrolysis reactor without requiring the use of a heat exchanger.

In a variation on this embodiment, the oxidation and hydrolysis reactions are conducted in different zones within the same reactor and/or in a mixed catalyst bed. Such a design may have the hydrolysis zone at the outlet of the reactor to prevent EO from exiting the reactor and ultimately passing into the carbon dioxide removal system.

In another variation on this embodiment, the hydrolysis catalyst can be composed of a mixture or zones of one or more different hydrolysis catalysts. For instance, a first zone may use a catalyst that is highly selective to MEG but with low conversion while a second zone may use a catalyst that is less selective to MEG but with very high activity.

In another variation on this embodiment, the hydrolysis reactor can comprise two separate hydrolysis reactors staged in a series or parallel fashion. The reactors can comprise the same or different hydrolysis catalysts. In the parallel system, the reactors can operate at the same time or in an alternating mode (e.g., one on-line and one off-line). This would allow for regeneration of the hydrolysis catalyst without shutting down production of mono-ethylene glycol.

Any material that is capable of promoting the oxidation of an alkene to an alkylene oxide can be used as the heterogeneous catalyst of the first step of the process, e.g., a silver-containing catalyst. The heterogeneous catalyst of the second step of the process is preferably at least one of modified and unmodified hydrotalcites, modified zeolites, metal phosphates, supported and unsupported metal salts, and ion-exchanged molecular sieves.

In a second embodiment, the invention is an improved gas phase process for the manufacture of alkylene glycol from the hydrolysis of alkylene oxide, the process comprising the step of contacting under gas phase hydrolysis conditions water and alkylene oxide (1) at a molar ratio of water to alkylene oxide of 0.5:1 to 20:1, and (2) over a heterogeneous catalyst comprising at least one of modified and unmodified hydrotalcites, modified zeolites, metal phosphates, supported and unsupported metal salts, and ion-exchanged molecular sieves.

In a third embodiment, the invention is a process in which the gaseous product from one alkene oxidation reactor or zone supplies feed for both an alkylene oxide hydrolysis reactor or zone and an alkylene oxide recovery and purification train. In this embodiment, the process comprises the steps of:

(A) Contacting in an alkene oxidation reactor or zone and under gas phase, oxidation conditions gaseous alkene and oxygen over a heterogeneous oxidation catalyst to produce a gaseous oxidation product comprising alkylene oxide, water and unreacted alkene;

(B) Dividing the gaseous oxidation product of (A) into a first stream and a second stream;

(C) Conveying the first stream of (B) to an alkylene oxide recovery and purification train in which alkylene oxide is at least partially absorbed into an absorbing medium and at least some of the alkylene oxide remains in the first stream of (B);

(D) Recovering and purifying alkylene oxide from the absorbing medium of (C);

(E) Recycling the alkylene oxide remaining in the first stream of (B) to the alkylene oxidation reactor or zone of (A);

(F) Conveying the second stream of (B) to an alkylene oxide hydrolysis reactor or zone;

(G) Contacting under gas phase, hydrolysis conditions the second stream of (B) with added water over a heterogeneous hydrolysis catalyst to produce a gaseous hydrolysis product of alkylene glycol and unreacted alkene:

(H) Conveying the gaseous hydrolysis product of (G) to an alkylene glycol recovery system, the system comprising one or more condensing zones or distillation columns to form a liquid fraction comprising alkylene glycol and water and an uncondensed gaseous fraction;

(I) Conveying the liquid fraction of (H) to an alkylene glycol recovery zone, e.g., a zone comprising one or more distillation columns, in which purified alkylene glycol is produced; and (J) Recycling the uncondensed gaseous hydrolysis product of (H) to the alkene oxidation reactor or zone of (A).

The process of this embodiment is typically conducted continuously, and the first and second streams of (B) are conveyed simultaneously to the alkylene oxide recovery and purification train and the alkylene oxide hydrolysis reactor or zone, respectively. The first and second streams can be the same or different in size, and the alkylene oxide recovery and purification train is typically the same as that used for the recovery and purification of alkylene oxide produced in an alkylene oxidation reactor not close-coupled to an alkylene oxide hydrolysis reactor. Moreover, the alkylene oxide and the alkylene glycol recovery and purification trains share the same carbon dioxide removal unit and cycle gas compressor and, as such, the same recycle gas loop.

In a fourth embodiment, the invention is a process in which the gaseous products from first and second alkene oxidation reactors and/or zones feed both an alkylene oxide recovery and purification train and an alkylene oxide hydrolysis reactor or zone. In this embodiment, the process comprises the steps of:

(A) Contacting in first and second alkene oxidation reactors or zones and under gas phase, oxidation conditions gaseous alkene and oxygen over a heterogeneous oxidation catalyst to produce, respectively, first and second gaseous oxidation products comprising alkylene oxide, water and unreacted alkene;

(B) Conveying the first gaseous oxidation product of (A) to an alkylene oxide recovery and purification train in which alkylene oxide is at least partially absorbed into an absorbing medium and at least some of the alkylene oxide remains in the first gaseous product of (A);

(C) Recovering and purifying alkylene oxide from the absorbing medium of (B);

(D) Recycling the unabsorbed alkylene oxide of the first gaseous product of (A) to either or both of the first and second alkene oxidation reactors or zones of (A);

(E) Conveying the second gaseous oxidation product of (A) to an alkylene oxide hydrolysis reactor or zone;

(F) Contacting under gas phase, hydrolysis conditions the second gaseous oxidation product of (A) with added water over a heterogeneous hydrolysis catalyst to produce a gaseous hydrolysis product of alkylene glycol and unreacted alkene;

(G) Conveying the gaseous hydrolysis product of (F) to an alkylene glycol recovery system, the system comprising one or more condensing zones or distillation columns to form a liquid fraction comprising alkylene glycol and water and an uncondensed gaseous fraction;

(H) Conveying the liquid fraction of (G) to an alkylene glycol recovery zone, e.g., a zone comprising one or more distillation columns, in which purified alkylene glycol is produced; and (I) Recycling the uncondensed gaseous hydrolysis fraction of (G) to either or both of the first and second alkene oxidation reactors or zones.

The process of this embodiment is typically conducted continuously, and the first and second gaseous oxidation products of (A) are conveyed simultaneously to the alkylene oxide recovery and purification train and the alkylene oxide hydrolysis reactor or zone, respectively. Typically, one alkene oxidation reactor feeds the alkylene oxide recovery and purification train, and the other alkene oxidation reactor feeds the alkylene oxide hydrolysis reactor. However, the alkene oxidation products of both alkene oxidation reactors can be divided such that each reactor feeds both the alkylene oxide recovery and purification train and the alkylene oxide hydrolysis reactor. The volume of the first and second gaseous alkylene oxidation products can be the same or different. The alkylene oxide recovery and purification train is typically the same as that used for the recovery and purification of alkylene oxide produced in an alkene oxidation reactor not close-coupled to an alkylene oxide hydrolysis reactor. Moreover, the alkylene oxide and the alkylene glycol recovery and purification trains share the same unreacted carbon dioxide recovery unit and cycle gas compressor and, as such, the same recycle gas loop.

DETAILED DESCRIPTION OF THE PREFERRED EMBODIMENT

Figure 1:
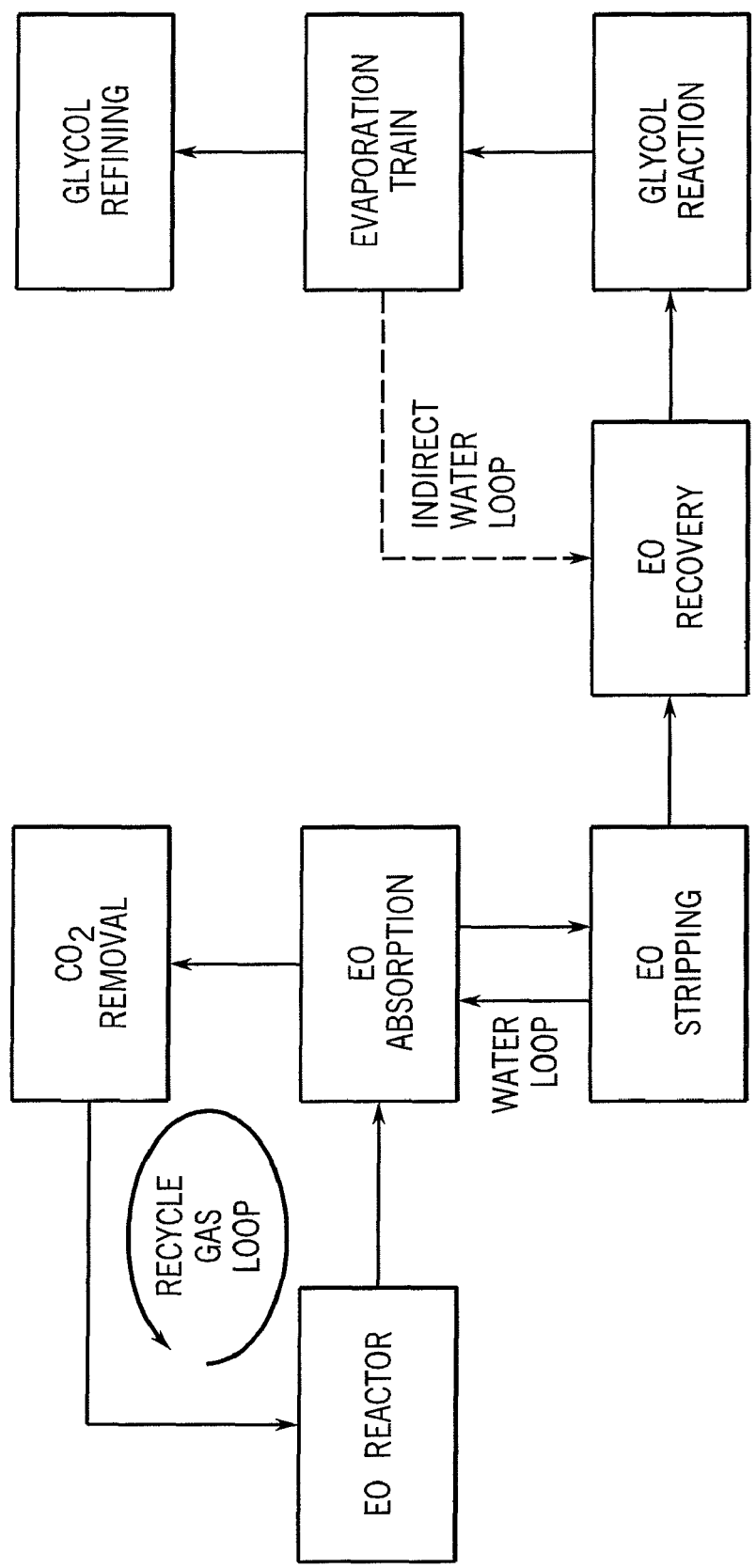
FIG. 1 is a schematic flow diagram of the conventional process for the manufacture of ethylene glycol from ethylene, oxygen and water.

All references to the Periodic Table of the Elements refer to the Periodic Table of the Elements, published and copyrighted by CRC Press, Inc., 2003. Also, any references to a Group or Groups shall be to the Group or Groups reflected in this Periodic Table of the Elements using the IUPAC system for numbering groups. Unless stated to the contrary, implicit from the context, or customary in the art, all parts and percents are based on weight and all test methods are current as of the filing date of this disclosure. For purposes of United States patent practice, the contents of any referenced patent, patent application, or publication are incorporated by reference in their entirety (or its equivalent US version is so incorporated by reference) especially with respect to the disclosure of synthetic techniques, definitions (to the extent not inconsistent with any definitions specifically provided in this disclosure) and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, melt index, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the relative amount of water and alkylene oxide in the alkylene oxide hydrolysis reaction mixture or mass, and various temperature and other process parameters.

The term "comprising" and its derivatives are not intended to exclude the presence of any additional component, step or procedure, whether or not the same is specifically disclosed. In order to avoid any doubt, all compositions claimed through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

As used with respect to a chemical compound, unless specifically indicated otherwise, the singular includes all isomeric forms and vice versa (for example, "hexane", includes all isomers of hexane individually or collectively). The terms "compound" and "complex" are used interchangeably to refer to organic-, inorganic- and organometal compounds. The term, "atom" refers to the smallest constituent of an element regardless of ionic state, that is, whether or not the same bears a charge or partial charge or is bonded to another atom. The term "heteroatom" refers to an atom other than carbon or hydrogen.

"Reaction mixture", "reaction mass" and like terms means the combination of materials necessary or ancillary to a reaction, typically under reactive conditions. Over the course of a reaction, a reaction mixture converts into a product mixture. Depending upon the moment in time in which the reaction mixture is characterized and other factors such as whether the process is batch or continuous, the physical state of the starting and product materials, etc., it will or can contain the reactants, catalyst, solvent, processing aids, products, byproducts, impurities and the like.

"Product mixture" and like terms means the combination of materials resulting from subjecting a reaction mixture to reaction conditions. A product mixture will always contain some product and/or byproduct and depending upon a multiplicity of factors (e.g., batch versus continuous, physical state of the starting materials, etc.), it may or may not contain unreacted starting materials, catalyst, solvent, processing aids, impurities, and the like. The typical product mixture of the oxidation reaction will contain alkylene oxide, oxygen and unreacted alkylene. The typical product mixture of the hydrolysis reaction will contain mono-alkylene glycol, di-alkylene glycol and higher alkylene glycol products, water, and unreacted alkylene, alkylene oxide and oxygen.

"Reaction conditions" and like terms generally refer to temperature, pressure, reactant concentrations, catalyst concentration, cocatalyst concentration, monomer conversion, product and by-product (or solids) content of the reaction mixture (or mass) and/or other conditions that influence the properties of the resulting product.

"Oxidation conditions" and like terms means the temperature, pressure, reactant concentrations, catalyst concentration, cocatalyst concentration, monomer conversion, product and by-product (or solids) content of the reaction mixture (or mass) and/or other conditions necessary to convert an alkene and oxygen to alkylene oxide.

"Hydrolysis conditions" and like terms mean the temperature, pressure, reactant concentrations, catalyst concentration and the like necessary to convert alkylene oxide and water to alkylene glycol.

"Continuous process" and like terms means that the process is operated at a steady state, i.e., the reactants are fed to the reactor or reaction zone at a rate substantially in balance with the rate that product is removed from the reactor or reaction zone such that the reaction mass in the reactor or reaction zone is relatively constant in volume and composition. Continuous process does not include a batch or semi-batch process, the former characterized by a depletion of reactants and a growth of product over time, and the latter typically characterized by the unbalanced addition of reactant and removal of product over time.

The alkene used in the first stage, i.e., the oxidation stage, of the present invention can be any aliphatic compound having at least one carbon-carbon double bond. Such compounds will generally contain from 2 to 25 carbon atoms and preferably from 3 to 12 carbon atoms, such as ethene (ethylene), propene (propylene), 1-butene, 2-butene, 1-pentene, 1-octene, 1-dodecene, styrene and methylstyrene. More preferably, however, ethylene and/or propylene are used as the alkene, thus producing ethylene oxide and/or propylene oxide. Ethylene is the most preferred alkene for use in this invention.

Oxygen can be used neat or diluted with one or more other gases, e.g., nitrogen, helium, methane, argon, water, carbon dioxide, etc. These other gases are preferably inert, i.e., non-reactive with the other reaction mixture components or itself, under the reaction conditions of the first stage, oxidation process. In some embodiments, a suitable oxygen-containing gas is air. In addition, the oxygen-containing gas can include gaseous promoters and/or gaseous byproduct inhibitors as later described.

The relative volumetric ratio of alkene to oxygen in the feed stock gas may range in accordance with any of such known conventional values. Typically, the volumetric ratio of alkene to oxygen in the feed stock varies from 2:1 to 6:1. Likewise, the quantity of inert gases, diluents, or other gaseous components such as water, carbon dioxide, and gaseous promoters and gaseous byproduct inhibitors, vary in accordance with known conventional ranges as found in the art.

The oxidation (epoxidation) reaction can be conducted in any suitable reactor, for example, fixed bed reactors, fixed bed tubular reactors, continuous stirred tank reactors (CSTRs), slurry phase reactors and fluid bed reactors, a wide variety of which are well known in the art. The desirability of recycling unreacted feed, employing a single-pass system, or using successive reactions to increase alkene conversion by employing reactors in a series arrangement can also be readily determined by those skilled in the art.

The particular mode of operation selected is dictated by, among other influences, process economics. Conversion of alkene, preferably ethylene, to alkylene oxide, preferably ethylene oxide, can be carried out, for example, by continuously introducing a feed stream containing alkene (e.g., ethylene) and oxygen, or an oxygen-containing gas, to a catalyst-containing reactor maintained at a temperature from 200° C. to 300° C., and a pressure maintained in a range from 5 atmospheres (506 kilopascals (kPa)) to 30 atmospheres (3040 kPa) depending on the mass velocity and productivity desired. Residence times in large scale reactors can be on the order of 0.1 to 5 seconds. The resulting alkylene oxide, preferably ethylene oxide, can then be forwarded directly to the hydrolysis reactor or separated and recovered from the reaction products using an alkylene oxide recovery and purification train.

The catalyst is an important factor in direct oxidation of an alkene to produce an alkylene oxide, e.g., ethylene to produce ethylene oxide. There are several well-known basic components of such catalysts: the active catalyst metal (generally silver for the oxidation of ethylene); a suitable support/carrier; and catalyst promoters, all of which can play a role in improving catalyst performance. These catalysts may be prepared with a carrier by impregnating the carrier with a solution of one or more compounds comprising an active metal, depositing the metal throughout the pores of the carrier, and then reducing the metal compound as is well known in the art, e.g., U.S. Pat. No. 6,511,938 and U.S. Pat. No. 5,187,140.

For the oxidation of ethylene or propylene, generally a carrier, e.g., an alpha-alumina or silica, is impregnated with a catalytic amount of silver, which is any amount of silver capable of catalyzing the direct oxidation of the alkylene with oxygen or an oxygen-containing gas to the corresponding alkylene oxide. In making such a catalyst, the carrier is typically impregnated (one or more times) with one or more silver compound solutions sufficient to allow the silver to be supported on the carrier in an amount greater than 5, more typically greater than 15 percent and even more typically greater than 30, percent by weight based on the weight of all of the components of the catalyst. Typically, the amount of silver supported on the carrier is less than 70 and preferably less than 50 percent by weight based on the weight of all of the components of the catalyst.

Although silver particle size in the finished catalyst is important, the range is not narrow. Suitable silver particle sizes are in the range of 10 to 10,000 angstroms in diameter. A preferred silver particle size is in the range of greater than 100 to less than 5,000 angstroms in diameter. The silver is desirably relatively uniformly dispersed within, throughout and/or on the carrier.

One or more of known promoters, i.e., materials which, when present in combination with particular catalytic materials, for example, silver, benefit one or more aspects of catalyst performance or otherwise act to promote the ability of the catalyst to make a desired product, for example ethylene oxide or propylene oxide, can also be used in the practice of this stage of the invention. Such promoters in themselves are generally not considered catalytic materials. The presence of such promoters in the catalyst is known to contribute to one or more beneficial effects on the catalyst performance, for example enhancing the rate or amount of production of desired product, reducing the temperature required to achieve a suitable rate of reaction, reducing the rates or amounts of undesired reactions, etc. Competing reactions occur simultaneously in the reactor, and a critical factor in determining the effectiveness of the overall process is the measure of control over these competing reactions. Something that is a promoter of one reaction can be an inhibitor of another reaction, for example a combustion reaction. Important is that the effect that the promoter has on the overall reaction is favorable to the efficient production of the desired product, for example ethylene oxide. The concentration of the one or more promoters present in the catalyst may vary over a wide range depending on the desired effect on catalyst performance, the other components of a particular catalyst, the physical and chemical characteristics of the carrier, and the oxidation (epoxidation) reaction conditions.

At least two types of promoters—solid promoters and gaseous promoters—exist. The solid and/or gaseous promoters are provided in a promoting amount. A "promoting amount" of a certain component of a catalyst refers to an amount of that component that works effectively to provide an improvement in one or more of the catalytic properties of that catalyst when compared to a catalyst not containing that component.

Examples of well-known solid promoters for catalysts used to produce ethylene oxide include compounds of potassium, rubidium, cesium, rhenium, sulfur, manganese, molybdenum, and tungsten. During the reaction to make ethylene oxide, the specific form of the promoter on the catalyst may be unknown. Examples of solid promoter compositions and their characteristics as well as methods for incorporating the promoters as part of the catalyst are described in U.S. Pat. No. 5,187,140, U.S. Pat. No. 6,511,938, U.S. Pat. No. 5,504,053, U.S. Pat. No. 5,102,848, U.S. Pat. Nos. 4,916,243, 4,908,343, 5,059,481, U.S. Pat. Nos. 4,761,394, 4,766,105, 4,808,738, 4,820,675, and 4,833,261.

The catalysts described in the preceding paragraphs are designed primarily for use in the gas phase oxidation of ethylene to ethylene oxide. As is well known in the art, most catalysts for the direct gas phase oxidation of ethylene to ethylene oxide do not give comparable results in the corresponding gas phase oxidation of the higher olefins, e.g., propylene. For the oxidation of these higher olefins, particularly propylene, other catalysts have been developed, are known in the art, and are exemplified in EP 0 318 815, U.S. Pat. Nos. 7,319,156, 5,770,746 and 5,698,719.

In the first embodiment of this invention, the oxidation reactor or zone effluent is passed to the hydrolysis reactor without recovery or purification of the alkylene oxide. This gaseous oxidation product is passed typically comprises between 0.1 and 20, preferably between 0.5 and 15 and more preferably between 1 and 5, weight percent (wt %) alkylene oxide.

One hallmark of this first embodiment of the invention is that the oxidation reactor is close-coupled with the hydrolysis reactor. "Close-coupled" and similar terms mean that the oxidation reactor and hydrolysis reactor are in open fluid communication with one another such that the effluent from the oxidation reactor is passed to an inlet of the hydrolysis reactor without undergoing alkylene oxide recovery and/or refinement.

Like the reactor for the oxidation reaction, the reactor for the hydrolysis reaction can also be of any design that will accommodate a gas phase reaction with a heterogeneous catalyst. It can be a single reactor, multiple reactors connected in series or in parallel, or one or more zones in a single reactor shell. Such reactors are typically equipped with feed inlets and product outlets, and may or may not be cooled externally. The hydrolysis reaction can be conducted in any suitable reactor, for example, fixed bed reactors, fixed bed tubular reactors, continuous stirred tank reactors (CSTRs) and fluid bed reactors, a wide variety of which are well known in the art. The reactor configuration can permit up-flow, down-flow or horizontal-flow of the reactants. One particularly suitable design is an adiabatic, down-flow, packed-bed reactor.

As noted above, the oxidation reaction produces byproduct water but the amount of byproduct water in the gaseous oxidation product is not a stoichiometric amount for the hydrolysis of the alkylene oxide to alkylene glycol. As such, water (liquid and/or steam) is added to the hydrolysis reactor such that the molar ratio of water to alkylene oxide is from 0.5:1 to 20:1, preferably from 0.9:1 to 10:1 and more preferably from 1:1 to 6:1. The exact amount of added water fed to the hydrolysis reactor depends, of course, on the specific operating parameters of the hydrolysis process, e.g., the amount of water in the gaseous oxidation product, the alkylene oxide, catalyst, temperature, flow velocity and the like.

The hydrolysis reaction proceeds uncatalyzed, however the presence of acids or bases enhances the rate of reaction. Acid and base catalysts, however, do have shortcomings. For instance, base catalysts are generally more selective to the formation of higher glycols and acid catalysts typically do not enhance the formation of mono-glycols. Hence, commercial processes typically utilize relatively neutral hydrolysis conditions (for instance, pH 6-10).

The art is replete with catalysts that are effective in promoting the hydration of an alkylene oxide to an alkylene glycol. These catalysts include but are not limited to fluorinated alkyl sulfonic acid ion exchange resins, carboxylic acids and halogen acids, strong acid cation exchange resins, acidic zeolites, alkali metal halides, organic tertiary amines, and various metal-containing compounds such as metal oxides. These catalysts are more fully described in U.S. Pat. No. 4,667,045 and the references cited within it.

In one embodiment the hydrolysis catalyst used in the practice of this invention is a heterogeneous catalyst that will promote the reaction between an alkylene oxide and water to obtain the corresponding alkylene glycol. This heterogeneous catalyst preferably is a solid catalyst disposed as a bed within the reactor or reaction zone. Preferably, the catalyst is at least one of a hydrotalcite, zeolite beta and metal phosphate. Representative examples of these catalysts include the Mg/Al hydrotalcites (and the metal exchanged hydrotalcites), metal-loaded zeolites, and metal phosphates. The catalysts used in this invention demonstrate a high degree of conversion and selectivity, typically at least 80% conversion of the alkylene oxide with 80% selectivity to mono-alkylene oxide (e.g., mono-ethylene glycol) at a water:alkylene oxide molar ratio (hydrolysis molar ratio) of 6:1 or lower. The catalyst activity and life are also strong.

The hydrolysis reaction is conducted at temperatures sufficient to enable the reaction between the alkylene oxide and water. The temperature, however, is not so great that the reagents are unduly adversely affected. Accordingly, the process is often carried out at a temperature between the dew point of the inlet gas stream of the glycol reactor and 300° C. Most often the reaction is carried out at a temperature between about 150° C. and 300° C. and for the hydrolysis of ethylene oxide, more preferably between 170° C. and 270° C.

The hydrolysis process can be conducted at sub-atmospheric, atmospheric or super-atmospheric pressure. However, the pressures employed are such that the alkylene oxide, water and most, if not all, products are maintained in the gaseous phase. For purposes of convenience, the reaction is typically conducted at pressures greater than ambient, e.g., between 0.1 and 1,000, and preferably between 2 and 100, kilograms per square centimeter ($kg/cm^2$) gauge.

The production of alkylene glycol according to this invention may be conducted in the presence of a gas, which is preferably inert. Gases which may be employed include air, carbon dioxide, nitrogen, argon and the like. Carbon dioxide is often present during the hydrolysis of alkylene oxide by the very nature of the process and the source of the alkylene oxide (especially by partial oxidation of alkylene, e.g., ethylene oxide). Frequently, the mole ratio of carbon dioxide to alkylene oxide is maintained at less than 0.1:1, particularly less than 0.05:1. Carbon dioxide can be used in certain amounts to enhance the selectivity provided by vanadate anion such as disclosed in U.S. Pat. No. 4,571,440.

The alkylene glycol may be recovered from the reaction effluent of the hydrolysis reactor in any convenient manner. Typically, the glycol is condensed in one or more heat exchangers, and then further refined by vacuum distillation.

Figure 2:
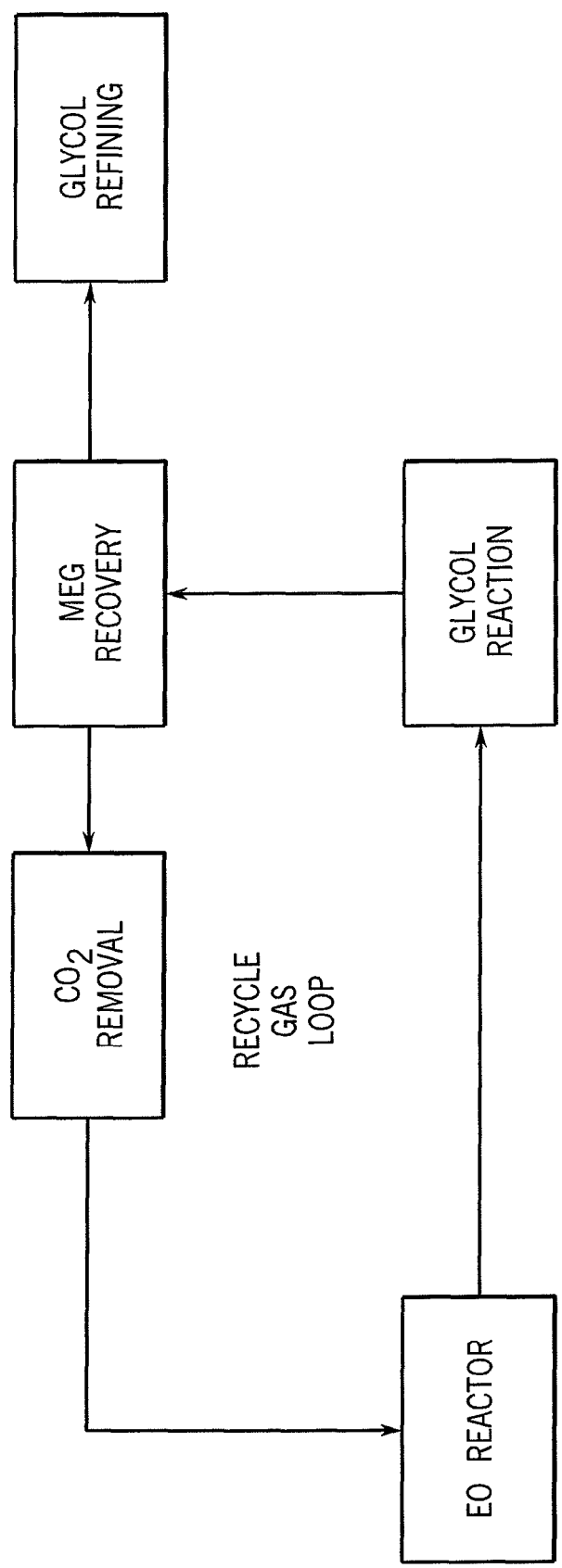
FIG. 2 is a schematic flow diagram of one embodiment of a two-stage, gas phase process for the manufacture of ethylene glycol from ethylene, oxygen and water.

FIG. 2 describes the first embodiment of the invention in the context of the production of mono-ethylene glycol (MEG) from ethylene, oxygen and water. Ethylene and oxygen are fed to a reactor in which ethylene is oxidized to ethylene oxide (EO). The reactor is configured and operated at conditions as described above. The total effluent, i.e., the oxidation product which is typically essentially completely gaseous but which may contain one or more liquid components, of the EO reactor is fed to the hydrolysis reactor and mixed with added water (not shown). As noted earlier, any gaseous component (other than the desired alkylene oxide) of this effluent can first be condensed and then fed to the hydrolysis reactor as a liquid or as a reconstituted gas, and any liquid component can be fed as a liquid, or first gasified and then fed as a gas. The hydrolysis reactor is configured and operated at conditions as previously described.

The glycol reaction produces a gaseous hydrolysis product that is passed to a separation unit in which the glycol products are separated from the gaseous hydrolysis product by condensation of the higher boiling components. The uncondensed gaseous hydrolysis product is then passed to a carbon dioxide removal unit before it is recycled back to the EO reactor (creating and closing a recycle gas loop). Various other equipment may be present in the cycle gas loop at locations obvious to those skilled in the art, such as compressors, heat exchangers and feed mixers, all of which are typically contained in the common recycle gas loop. The glycol product typically comprises a majority of MEG and a minority of other glycols, e.g., di-ethylene glycol, tri-ethylene glycol, tetra-ethylene glycol and heavier products, and is subjected to further recovery and refinement, e.g., a series of distillation steps, to separate and recover these products either individually or as one or more mixtures.

Figure 3:
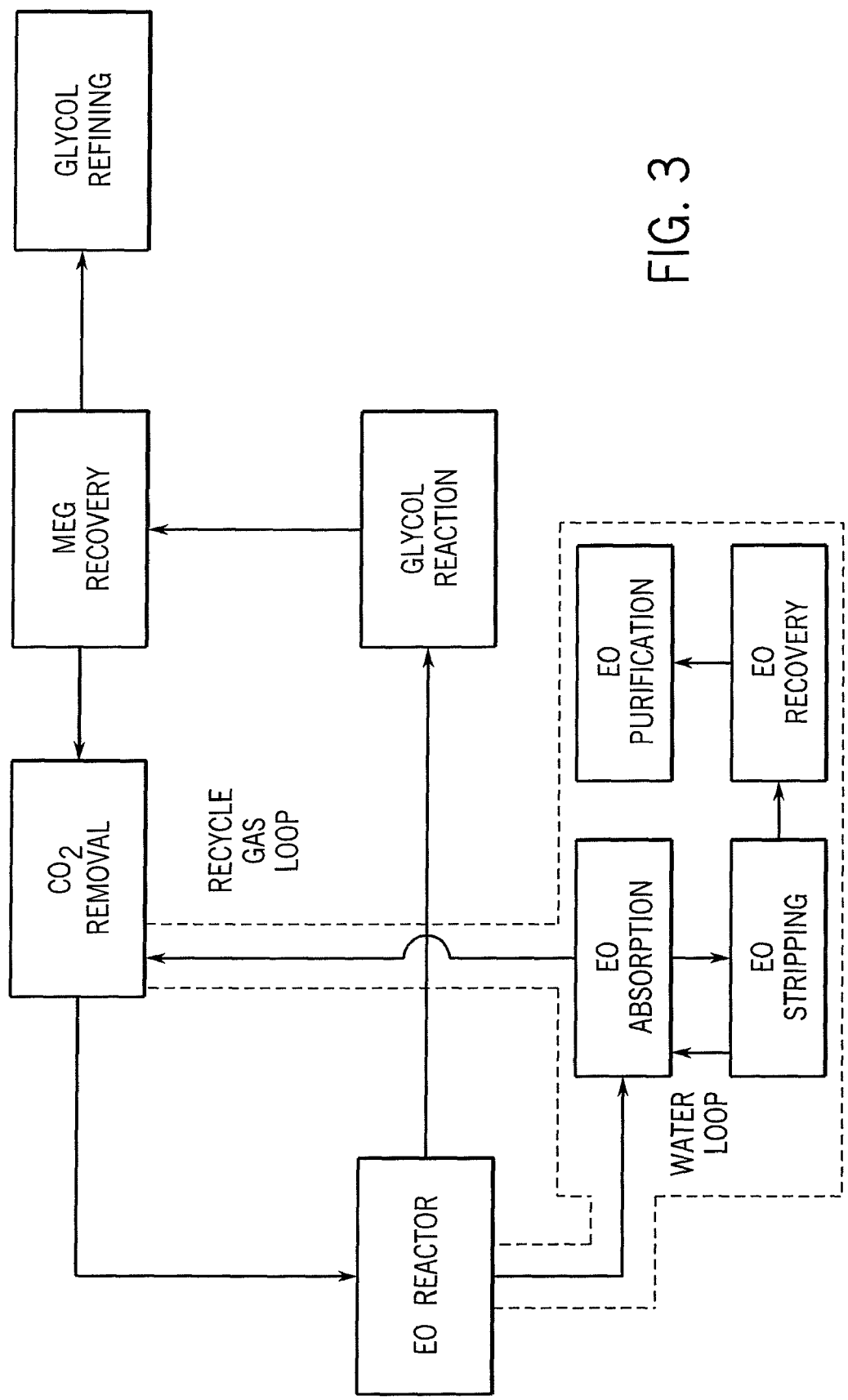
FIG. 3 is a schematic flow diagram of an embodiment of a two-stage, gas phase process for the manufacture of ethylene glycol from ethylene, oxygen and water in which one alkylene oxidation reactor feeds both an alkylene oxide recovery and purification train and an alkylene oxide hydrolysis reactor or zone.

FIG. 3 describes the third embodiment of the invention also in the context of the production of MEG from ethylene, oxygen and water. This embodiment differs from the first embodiment in that the gaseous oxidation product is divided by any suitable means, e.g., two or more oxidation reactor outlets, baffles, a slip stream pipe off of the main pipe carrying the oxidation product, etc., such that part of the oxidation product is delivered to the hydrolysis reactor and part of the oxidation product is delivered to an ethylene oxide recovery and purification train. The amount of oxidation product delivered to one destination relative to the amount delivered to the other destination can vary to convenience. The size of the hydrolysis reactor and both the ethylene oxide recovery and purification trains are sized proportional to the size of their respective feed streams, although some variation in reactor sizes can be present to account for some change in purified ethylene oxide to glycol product ratio. The hydrolysis reactor and both the ethylene oxide and ethylene glycol recovery and purification trains operate as described above. One hallmark of this embodiment is that the both the ethylene oxide and glycol recovery and purification trains share the recycle gas loop, and thus enjoy reduced capital and operating expense as compared to the total of two separate trains. In this particular embodiment, the link between the two trains is the shared unit in which unreacted ethylene is recovered and recycled.

Figure 4:
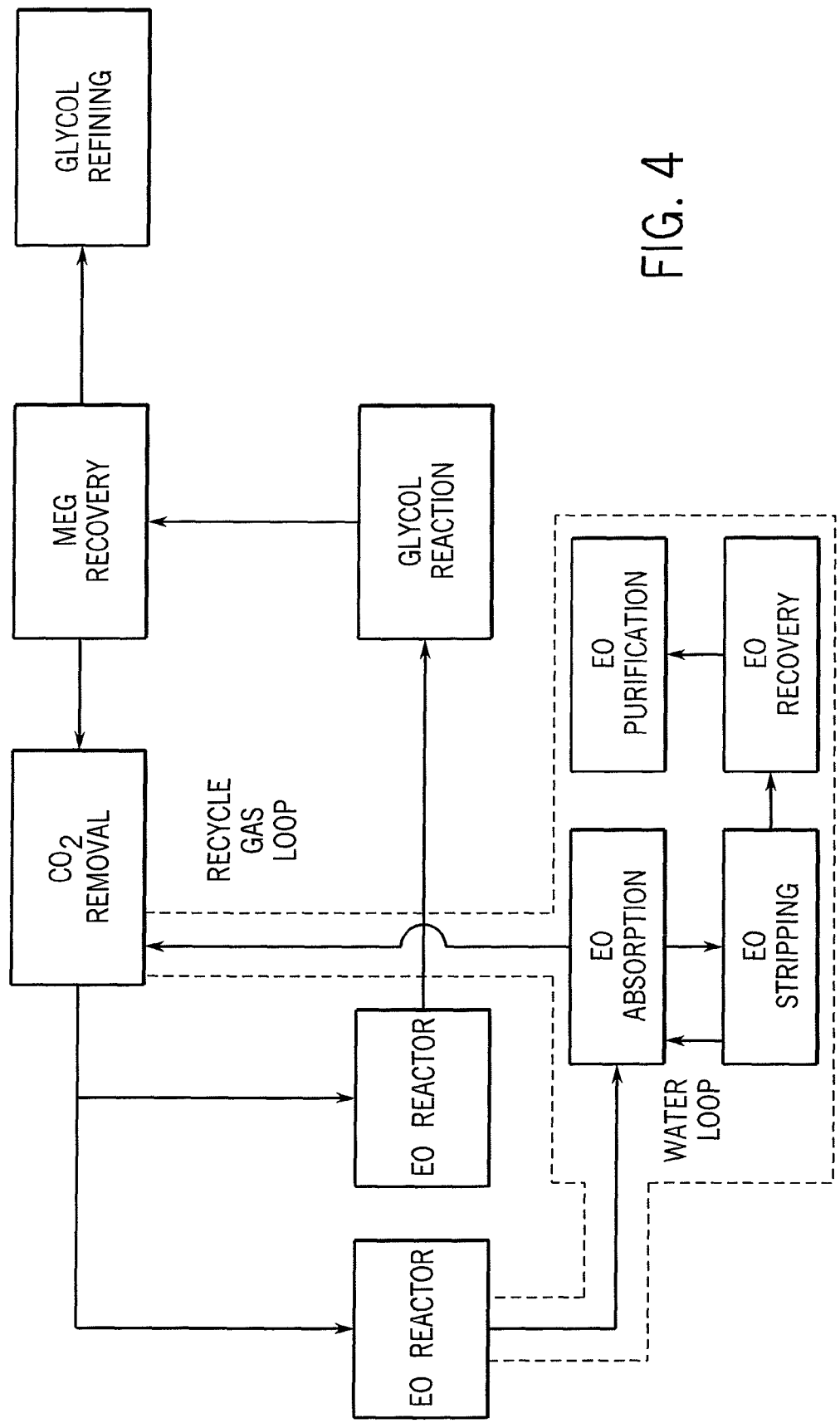
FIG. 4 is a schematic flow diagram of an embodiment of a two-stage, gas phase process for the manufacture of ethylene glycol from ethylene, oxygen and water in which one alkylene oxidation reactor or zone feeds an alkylene oxide recovery and purification train, and a second alkylene oxidation reactor feeds an alkylene oxide hydrolysis reactor or zone.

FIG. 4 describes the fourth embodiment of the invention also in the context of the production of MEG from ethylene, oxygen and water. This embodiment differs from the first and third embodiment in that two oxidation reactors are operated in parallel. Both reactors operate as described above. One reactor provides feed for the ethylene oxide recovery and purification train, and the other reactor provides feed for the hydrolysis reactor. In a variation on this embodiment, one or both reactors can provide feed to both the ethylene oxide recovery and purification train and the hydrolysis reactor. The amount of oxidation product delivered to the hydrolysis reactor relative to the amount delivered to the ethylene oxide recovery and purification train can vary to convenience. The size of the hydrolysis reactor and both the ethylene oxide recovery and purification trains are sized proportional to the size of their respective feed streams, although some variation in reactor sizes can be present to account for some change in purified ethylene oxide to glycol product ratio. The hydrolysis reactor and both the ethylene oxide and ethylene glycol recovery and purification trains also operate as described above. As in the third embodiment, both the ethylene oxide and glycol recovery and purification trains share the recycle gas loop.

The following examples are provided to assist in the understanding of the invention, and they are not intended as a limitation on the invention. All percentages and parts of solid are by weight, and all percentages and parts of liquids and gases are by volume, unless otherwise indicated.

Specific Embodiments

General Synthesis and Materials.

All gas mixture cylinders of ethylene oxide (EO), ethylene and $N_2$ are purchased from Air Gas and analyzed versus an external calibration standard purchased from Air Gas (all cylinders contain a certificate of analysis measured gravimetrically and are reported in mol %). Carbon dioxide ($CO_2$) gas cylinders are purchased from Airgas and used as received. Carbon binder is obtained from Chemplex Industries and used as received. Molecular sieve absorbent is purchased from the Kurt J. Lesker Company in ¼ inch extrudates. Zeolite beta is purchased from Zeolyst International. All pellets and extrudates are crushed and sieved through 24×40 or 16×30 mesh screens prior to use unless otherwise noted. All other reagents are purchased from the Aldrich Chemical Company and used as received unless otherwise noted.

Catalyst Synthesis

Hydrotalcites: Sodium hydroxide (NaOH) and sodium carbonate ($Na_2CO_3$) are dissolved in deionized water in a pint glass bottle equipped with a stirbar. Hydrated magnesium nitrate ($Mg(NO_3)_2 \cdot 6H_2O$), hydrated aluminum nitrate ($Al(NO_3)_3 \cdot 9H_2O$) and the corresponding metal nitrate are dissolved in deionized water, charged into a 250 ml Erlenmeyer flask, and added drop-wise to the $NaOH/Na_2CO_3$ solution while vigorously stirring. After complete addition, the stirring is discontinued and the glass bottle is sealed and heated at 70° C. for 16 hours. The mixture is allowed to cool to room temperature and a solid precipitate is recovered by vacuum filtration. The solid is washed with deionized water (3×, 50 mL) and dried in vacuo at 100° C. The resulting solid is crushed and sieved through 24×40 or 16×30 mesh screens.

Cs βeta: Cesium hydroxide (CsOH) is dissolved with warm water and charged into an additional funnel. H-β(eta) and water are added into a 500 mL Fisher-Porter tube equipped with a stirbar and vigorously stirred. The aqueous CsOH solution is added drop-wise to the Fisher-Porter tube over 20 minutes. After complete addition, the Fisher-Porter tube is sealed and stirred at room temperature for 5 hours. The stirring is discontinued and the vessel is placed inside a 100° C. oven and heated for 12 hours. The vessel is removed from the oven and allowed to cool to room temperature. A white solid is collected by vacuum filtration, washed with water (3×, 50 mL), calcined at 600° C. for 12 hours and crushed and sieved through 16×30 mesh screens.

$CsNO_3$/Cs Impregnated Molecular Sieve Absorbent: Using an incipient wetness technique, molecular sieve extrudates are added to an aqueous solution of $CsNO_3$ and allowed to sit at room temperature for 2 hours. The solid is dried in vacuo at 50° C. overnight. The solid is crushed and sieved through 24×40 mesh screens (half the material is calcined at 600° C. for 12 hours).

Formation of Pellets for Catalyst Screening: Powdered catalysts (5 g) and graphite binder (briquette grade, 0.25 g) are placed inside a 20 mL vial. If necessary more graphite is added to ensure adequate pellet crush strength. The catalyst and binder are mixed on a mini vortexer for 2 minutes. The solid mixture is placed in a circular, stainless steel cast dye (radius of 3 mm, depth of 5 mm) and pressed at 24,000 pounds on a Carver Hydraulic Press for 2-12 hours. Using a mortar and pestle, the resulting pellet is crushed and then sieved through 24×40 or 16×30 mesh screens.

General Reactor Procedure:

One-half gram (0.5 g) of catalyst is packed in ¼" thick-walled stainless steel tubing and placed in an oven set at the desired temperature. The inlet gas feed typically contains 1.5 mol % ethylene oxide. This is mixed with the required amount of water, vaporized and fed to the reactor. The concentration of ethylene at the inlet and outlet of the reactor are monitored using a process gas chromatograph. Catalysts are tested by passing a gas stream of 1.5% EO, 0% or 1.5% $CO_2$, 20% ethylene and $N_2$ (balance) at 250 psi, hydrolysis ratio (w/w) 2.5, reaction temperatures ranging from 190-250° C. and gas hourly space velocity (GHSV) of 4,000/hr (½) or 8,000/hr (1) over packed catalyst reactor beds. A condenser at the outlet of the reactor condenses the heavy products (typically mono-ethylene glycol and highers). The composition of this condensate is measured with a laboratory gas chromatograph.

The EO conversion is based on the values of EO from the inlet and outlet of each reactor. Gas chromatograms of the outlet samples are taken using a HP-6890 GC equipped with a flame ionization detector (FID) detector and a DB-1701 capillary column. GC samples are analyzed by taking aliquots (2-3 mL) of the reaction outlet sample. Reaction product concentrations are quantified versus an external standard on GC.

The GC method is setup to measure mono-ethylene glycol (MEG), diethylene glycol (DEG), triethylene glycol (TEG), tetraethylene glycol (TTEG) and ethylene carbonate (EC). All other peaks are lumped together as unknowns. MEG selectivity is defined as glycol selectivity and calculated from the GC area percentage of MEG divided by the sum of the GC area percentages of MEG, DEG, TEG and TTEG.

The MEG efficiency is defined as the percentage of MEG versus all the organic reaction products from EO, ethylene or $CO_2$ and is calculated from the GC area percentage of MEG divided the sum of the GC area percentages of all the components found in the GC trace (equation 2).

Table 1 presents examples of various inventive catalysts with high activity and selectivity.

TABLE 1

High Activity and Selectivity Catalysts

| Catalyst | Temp (° C.) | Flow Rate | Conversion (%) | Unknown (wt %) | MEG Selectivity % | MEG Efficiency % |
|---|---|---|---|---|---|---|
| Hydrotalcite (3/1 Mg/Al) | 190 | 1 | 80 | 0.5 | 88 | 88 |
| Hydrotalcite - Fe (3/1 Mg/Al) | 210 | 1 | 100 | 0 | 95 | 95 |
| Hydrotalcite - Ag (3/1 Mg/Al) | 210 | 1 | 90 | 2.8 | 91 | 89 |
| Hydrotalcite - Co (3/1 Mg/Al) | 230 | ½ | 90 | 0.3 | 86 | 864 |
| Cs on Molecular Absorbent | 230 | ½ | 74 | 2.4 | 85 | 83 |
| Molecular Sieve Absorbent | 230 | ½ | 73 | 1.5 | 71 | 70 |
| Cs Zeolite βeta | 265 | ½ | 93 | 0 | 97 | 97 |
| $La(PO_4)_3$ | 230 | ½ | 100 | 8.6 | 78 | 71 |

Three catalyst families afford high activity and selectivity, i.e., hydrotalcites, zeolite and metal phosphates. The hydrotalcites are highly active for EO hydrolysis and form minimal unknown by-products during the reaction. Calcined hydrotalcite catalysts are less active than uncalcined hydrotalcites. Certain metal ions incorporated into the hydrotalcite or zeolite catalyst structure improve performance.

The most ideal catalyst for gas-phase EO hydrolysis is a stable, heterogeneous compound that converts 100% EO to 100% MEG with a catalyst life of at least 18 months. Catalysts that demonstrate 80% EO conversion to 80% MEG or better, e.g., 90% EO conversion to 85% MEG, are very desirable for commercial applications.

Pilot Plant Catalyst Screening

Zeolite beta in extrudate form is tested in a pilot plant reactor system using an EO feed gas. The zeolite beta is uncalcined, unpromoted and comprises silicon and alumina at a Si/Al ratio of 150:1. Over a five day run the reactor is set to run at 190° C. at 175 psig backpressure for the first day; the backpressure is increased to 250 psig on the second day; the reactor temperature is raised to 210° C. on the third day; and the temperature is raised again to 230° C. on the fourth day. The EO conversion is between 75 and 80% for the first part of the run, but tapers off as the run progresses. Carbon dioxide and ethylene concentration at the reactor outlet is fairly constant throughout the run at about 1.35 mole percent and 23.5 mole percent, respectively. The results of the run are reported in Table 2.

TABLE 2

Selectivity (%) of Unpromoted Zeolite Beta

| Day | MEG | DEG | TEG | TTEG | Unknowns |
|---|---|---|---|---|---|
| 1 | 51.8 | 27.9 | 9.9 | 3.7 | 3.7 |
| 2 | 52.3 | 29.3 | 9.5 | 2.8 | 2.8 |
| 3 | 59.1 | 24.4 | 8.7 | 2.8 | 1 |
| 4 | 27.1 | 24 | 8.6 | 1.9 | 15.6 |

Analysis of the product samples shows that the catalyst is not very selective to monoethylene glycol (MEG). The MEG selectivity for the first three days is between 51.8 and 59.1 percent, but drops off sharply in the fourth day (27.1%). Higher glycol (diethylene glycol (DEG), triethylene glycol (TEG) and tetraethylene glycol (TTEG) are also elevated.

Cesium-promoted zeolite beta in extrudate form is tested in a pilot plant reactor system using an EO feed gas. The reactor is set to 200° C. and 300 psig backpressure, and water is set to provide a hydrolysis ratio of 2:1 w/w. The EO conversion initially started off at about 60% and began to improve as the run progressed reaching about 75% at the end of a day. The product sample obtained is clear and the MEG selectivity relative to the unpromoted zeolite beta is much improved as shown in Table 3.

TABLE 3

Selectivity (%) of Cs-promoted Zeolite Beta

| Day | MEG | DEG | TEG | TTEG | Unknowns |
|---|---|---|---|---|---|
| 1 | 86.6 | 7.1 | 2.0 | 0.9 | 1.2 |

Sliver-promoted hydrotalcite (calcined) is run in the pilot plant. The hydrotalcite comprises Mg/Al at a 3:1 ratio. The system is heated to 200° C. under nitrogen before water and EO are fed to the reactor. Over a five day run the reactor is set to run at 150° C. at 175 psig backpressure for the first day; the backpressure is increased to 250 psig on the second day; the reactor temperature is raised to 170° C. on the third day; and the temperature is raised again to 190° C. on the fourth day. The results of the run are reported in Table 4.

TABLE 4

Selectivity (%) of Ag-Promoted Mg/Al Hydrotalcite (Calcined)

| Day | MEG | DEG | TEG | TTEG | Unknowns |
|---|---|---|---|---|---|
| 1 | 74 | 16 | 6 | 2.6 | 1.4 |
| 2 | 82.7 | 12.5 | 3.5 | 1.3 | 0 |
| 3 | 85 | 11.8 | 2.5 | 0.8 | 0 |
| 4 | 84.8 | 11.9 | 2.3 | 0.6 | 0.3 |

The selectivity for the calcined 3:1 Mg/Al hydrotalcite with Ag is higher on average than the uncalcined version of the same catalyst (values of the uncalcined version of the catalyst not reported here).

Screening Reactor Data

Table 5 reports the results of using metal phosphates, and Table 6 reports the results of using 3-angstrom molecular sieves, to catalyze the gas phase hydration of ethylene oxide to ethylene glycol. The carbon dioxide/ethylene oxide molar ratio and water/ethylene oxide molar ratio was 5 in all runs. The reaction temperature of the runs using the metal phosphates was 190° C. and 230° C. for the runs using the molecular sieves. As the data shows, not all metals perform well but some deliver a very desirable combination of conversion and selectivity, e.g., $BPO_4$ and $Ag_3PO_4$.

TABLE 5

Conversion (%) and Selectivity (%) of Metal Phosphate Hydrolysis Catalysts

| Catalyst | Conversion (Mole %) | MEG | DEG | TEG | TTEG | Unknowns |
|---|---|---|---|---|---|---|
| $BPO_4$ | 100 | 75 | 18 | 3 | 0 | 4 |
| $AlPO_4$ | 75 | 61 | 24 | 7 | 3 | 5 |
| $FePO_4$ | 70 | 52 | 18 | 10 | 4 | 16 |
| $K_3PO_4$ | * | NA | NA | NA | NA | NA |
| $Na_3PO_4$ | * | NA | NA | NA | NA | NA |
| $Ag_3PO_4$ | 83 | 72 | 17 | 5 | 2 | 4 |

*No significant conversion.
NA—Not applicable.

TABLE 6

Conversion (%) and Selectivity (%) of Metal-Promoted 3-Angstrom Molecular Sieve Hydrolysis Catalysts

| Metal Promoter | Conversion (Mole %) | MEG |
|---|---|---|
| Barium | 43 | 98.5 |
| Potassium | * | NA |
| Silver | 40 | 98.1 |
| Cobalt | 32 | 97 |

* No significant conversion.
NA—Not applicable.

Although the invention has been described in considerable detail by the preceding examples and references to the drawings, this detail is for the purpose of illustration and is not to be construed as a limitation upon the spirit and scope of the invention as it is described in the appended claims. All patents and publications cited above, specifically including for U.S. practice all U.S. patents, allowed patent applications and U.S. Patent Application Publications, are incorporated herein by reference.

What is claimed is:

1. A two-stage, gas phase process for manufacturing alkylene glycol from an alkene, oxygen and water, the process comprising the steps of:
   (A) Contacting under gas phase, oxidation conditions gaseous alkene and oxygen over a heterogeneous oxidation catalyst to produce a gaseous oxidation product comprising alkylene oxide, water and unreacted alkene;
   (B) Contacting under gas phase, hydrolysis conditions the gaseous oxidation product of (A) with added water over a heterogeneous hydrolysis catalyst to produce a gaseous alkylene glycol and unreacted alkene; and
   (C) Recycling the unreacted alkene of (B) to (A).

2. A process in which the gaseous product from one alkene oxidation reactor or zone supplies feed for both an alkylene oxide hydrolysis reactor or zone and an alkylene oxide recovery and purification train, the process comprises the steps of:
   (A) Contacting in an alkene oxidation reactor or zone and under gas phase, oxidation conditions gaseous alkene and oxygen over a heterogeneous oxidation catalyst to produce a gaseous oxidation product comprising alkylene oxide, water and unreacted alkene;
   (B) Dividing the gaseous oxidation product of (A) into a first stream and a second stream;
   (C) Conveying the first stream of (B) to an alkylene oxide recovery and purification train in which alkylene oxide is at least partially absorbed into an absorbing medium and at least some of the alkylene oxide remains in the first stream of (B);
   (D) Recovering and purifying alkylene oxide from the absorbing medium of (C);
   (E) Recycling the alkylene oxide remaining in the first stream of (B) to the alkylene oxidation reactor or zone of (A);
   (F) Conveying the second stream of (B) to an alkylene oxide hydrolysis reactor or zone;
   (G) Contacting under gas phase, hydrolysis conditions the second stream of (B) with added water over a heterogeneous hydrolysis catalyst to produce a gaseous hydrolysis product of alkylene glycol and unreacted alkene:
   (H) Conveying the gaseous hydrolysis product of (G) to an alkylene glycol recovery system, the system comprising one or more condensing zones to form a liquid fraction comprising alkylene glycol and water and an uncondensed gaseous fraction;
   (I) Conveying the liquid fraction of (H) to an alkylene glycol recovery zone in which purified alkylene glycol is produced; and
   (J) Recycling the uncondensed gaseous hydrolysis product of (H) to the alkene oxidation reactor or zone of (A).

3. A process in which the gaseous products from first and second alkene oxidation reactors and/or zones feed both an alkylene oxide recovery and purification train and an alkylene oxide hydrolysis reactor or zone, the process comprises the steps of:
   (A) Contacting in first and second alkene oxidation reactors or zones and under gas phase, oxidation conditions gaseous alkene and oxygen over a heterogeneous oxidation catalyst to produce, respectively, first and second gaseous oxidation products comprising alkylene oxide, water and unreacted alkene;
   (B) Conveying the first gaseous oxidation product of (A) to an alkylene oxide recovery and purification train in which alkylene oxide is at least partially absorbed into an absorbing medium and at least some of the alkylene oxide remains in the first gaseous product of (A);
   (C) Recovering and purifying alkylene oxide from the absorbing medium of (B);
   (D) Recycling the unabsorbed alkylene oxide of the first gaseous product of (A) to either or both of the first and second alkene oxidation reactors or zones of (A);
   (E) Conveying the second gaseous oxidation product of (A) to an alkylene oxide hydrolysis reactor or zone;
   (F) Contacting under gas phase, hydrolysis conditions the second gaseous oxidation product of (A) with added water over a heterogeneous hydrolysis catalyst to produce a gaseous hydrolysis product of alkylene glycol and unreacted alkene;
   (G) Conveying the gaseous hydrolysis product of (F) to an alkylene glycol recovery system, the system comprising one or more condensing zones to form a liquid fraction comprising alkylene glycol and water and an uncondensed gaseous fraction;
   (H) Conveying the liquid fraction of (G) to an alkylene glycol recovery zone in which purified alkylene glycol is produced; and
   (I) Recycling the uncondensed gaseous hydrolysis fraction of (G) to either or both of the first and second alkene oxidation reactors or zones.

4. The process of claim 1 conducted continuously.

5. The process of claim 4 in which the alkylene is at least one of ethylene and propylene, and the alkylene oxide is at least one of ethylene oxide and propylene oxide.

6. The process of claim 5 in which the alkylene oxide and hydrolysis processes share a common recycle loop comprising a carbon dioxide removal unit.

7. The process of claim 6 in which the hydrolysis catalyst is selected from the group consisting of hydrotalcites, metal impregnated zeolite, phosphates, and ion-exchanged molecular sieves.

8. The process of claim 7 in which the hydrotalcite comprises Mg and Al at a 3:1 molar ratio.

9. The process of claim 8 in which the hydrotalcite is doped with at least one of iron, cobalt or silver.

10. The process of claim 2 conducted continuously.

11. The process of claim 10 in which the alkylene is at least one of ethylene and propylene, and the alkylene oxide is at least one of ethylene oxide and propylene oxide.

12. The process of claim 11 in which the alkylene oxide and hydrolysis processes share a common recycle loop comprising a carbon dioxide removal unit.

13. The process of claim 12 in which the hydrolysis catalyst is selected from the group consisting of hydrotalcites, metal impregnated zeolite, phosphates, and ion-exchanged molecular sieves.

14. The process of claim 13 in which the hydrotalcite comprises Mg and Al at a 3:1 molar ratio.

15. The process of claim 14 in which the hydrotalcite is doped with at least one of iron, cobalt or silver.

16. The process of claim 3 conducted continuously.

17. The process of claim 16 in which the alkylene is at least one of ethylene and propylene, and the alkylene oxide is at least one of ethylene oxide and propylene oxide.

18. The process of claim 17 in which the alkylene oxide and hydrolysis processes share a common recycle loop comprising a carbon dioxide removal unit.

19. The process of claim 18 in which the hydrolysis catalyst is selected from the group consisting of hydrotalcites, metal impregnated zeolite, phosphates, and ion-exchanged molecular sieves.

20. The process of claim 19 in which the hydrotalcite comprises Mg and Al at a 3:1 molar ratio.

* * * * *